United States Patent [19]

McDowell et al.

[11] Patent Number: 5,674,189

[45] Date of Patent: Oct. 7, 1997

[54] DRESSING GUARD

[76] Inventors: Charles Edward McDowell; Mary Frances McDowell, both of 1736 Still Water Glen, Escondido, Calif. 92026

[21] Appl. No.: 536,681

[22] Filed: Sep. 27, 1995

[51] Int. Cl.⁶ .................. A61F 13/00; A41D 13/08
[52] U.S. Cl. .................. 602/62; 602/63; 604/304; 604/308; 2/16
[58] Field of Search .................. 604/304–308; 602/20, 61–62, 60; 606/54–55; 128/DIG. 20; 2/16, 910, 912, 916

[56] References Cited

U.S. PATENT DOCUMENTS

| | | | |
|---|---|---|---|
| 1,304,558 | 5/1919 | Grau | 604/308 |
| 3,934,582 | 1/1976 | Gorrie | 602/62 |
| 4,146,021 | 3/1979 | Brosseau et al. | 602/62 |
| 5,168,577 | 12/1992 | Detty | 602/62 |
| 5,178,614 | 1/1993 | McDowell et al. | 604/332 |
| 5,181,274 | 1/1993 | DeFiore | 2/46 |
| 5,362,306 | 11/1994 | McCarver et al. | 602/60 |
| 5,417,646 | 5/1995 | Gauvry | 602/62 |
| 5,419,757 | 5/1995 | Daneshvar | 604/304 |

FOREIGN PATENT DOCUMENTS 965324   4/1975   Canada .................. 128/56

Primary Examiner—John G. Weiss
Assistant Examiner—David J. Cho
Attorney, Agent, or Firm—Gene Scott—Patent Law & Venture Group

[57] ABSTRACT

A body shielding device having an elongate tube constructed of flexible, water-resistant sheet material. The tube has a diameter large enough to allow a limb to be inserted through the tube. The tube preferably has a permanent crease running along the length of the tube so as to allow a sidewall of the tube to be easily folded over itself as needed to accomodate varying limb sizes. Fastening strips are provided on the outer surface of the tube to provide convenient means by which to secure the tube tightly around the limb in the folded-over position.

5 Claims, 1 Drawing Sheet ic # DRESSING GUARD

BACKGROUND OF THE INVENTION

1. Field of the Invention

This invention relates generally to body shielding devices and more particularly to a water-resistant guard designed to fully encircle and protect a given area of the body, such as an arm, leg or torso, from exposure to moisture, bacteria and the like.

2. Description of Related Art

Invention and use of body shielding devices are well known in the art, as they are commonly employed to protect a given area of the body from exposure to air, water, wind or the like. Typically, these guards have either a relatively loose-fitting configuration designed to cover a large surface area or a very tight-fitting configuration designed solely to cover the desired area.

The loose-fitting guards generally provide means by which to tighten the guard around a given area of the body so that a single guard can be employed to protect a variety of different body shapes and sizes. For example, Dunbar Canadian patent 0965324 discloses a shield having a trapezoidally-shaped sheet of material which is secured to the wearer by an upper detachable belt which encircles the lower part of the wearer's trunk, and a lower detachable belt which encircles the wearer's upper thigh. The sheet is gathered along its side edges to provide fullness so that there is enough room for a dressing to be placed underneath it.

De Diore U.S. Pat. No. 5,181,274 discloses a shield particularly designed for protecting a catheter while a patient is bathing. The shield includes a band for engaging a portion of the patient's body and a second band for engaging another portion of the patient's body. A waterproof panel extends between the bands, and water absorbent panels extend between the bands on lateral sides of the water proof panel.

While these loose-fitting, adjustable shield configurations have proven to be somewhat useful, they are plagued with several problems. First of all, although they generally provide means by which to tighten the guard around the body as needed, they provide no means by which to seal the guard around the area to be protected. Thus, such guards provide only limited protection, as any movement or change in position may cause the guard to temporarily move out of position, thus allowing water or the like to contact the area. Yet another problem with such configurations is that although the entire device can be tightened to fit around a limb as needed, the actual area covering the wound is of a fixed size, thus limiting the potential uses of the guard.

The prior art devices having a form-fitting configuration are generally shaped and sized to fit exactly over a particular portion of the body. For example, Mc Dowell et. al U.S. Pat. No. 5,178,614 is essentially a small, rigid, thin outwardly convex shell which is designed to directly attach to the exterior of the body by means of adhesive. This device is particularly designed to cover a stoma pouch, and, as such, is shaped and sized in accordance with standard pouches.

These devices provide more protection than loose-fitting configurations, as they fit tightly around a given area, thus ensuring maximum protection regardless of the wearer's movements. However, such guards are significantly limited in that they are shaped and sized to fit over a particular part of the body, and thus cannot be easily adapted for other uses. This requires that different shields be purchased for each different area of the body that needs protection. In addition, these close-fitting guards are generally not adjustable and do not therefore accommodate differing body sizes.

Thus there is a clear need for an improved guard that is able to effectively protect an area of the body regardless of the person's position or movement. Such a guard would be easily adjustable to fit tightly around a variety of different body parts and sizes, thus allowing a single guard to be in a wide variety of different applications. The present invention fulfills these needs and provides further related advantages as described in the following summary.

SUMMARY OF THE INVENTION

The present invention is an improved body guarding device that is designed to more easily and effectively protect a portion of the body. The guard is particularly useful in covering the dressings over burns, cuts, casts, sutures and other such wounds. The present invention consists generally of an elongated, open-ended tube constructed of lightweight, flexible, water resistant material. The tube has a diameter great enough to allow a given body part to be inserted through the tube and a length great enough to ensure that the area to be protected is completely covered by the tube. Thus it is a primary object of the present invention to provide a guard that completely encircles a given area of the body, thus more fully protecting that area of the body from exposure to water, bacteria and the like. The tube has a series of fastening strips on its outer surface that allow the tube to be easily secured in a folded over position so that the tube diameter is decreased to fit tightly around the area of the body. This is a significant advantage over loose-fitting prior art devices in that it can be adjusted to conform closely to the contour of any given area to be protected and is thus not affected by the wearer's movement. Likewise, the present inventive construction provides a significant improvement over prior art tight-fitting devices in that the present invention can be adjusted so as to fit tightly around a wide variety of different objects, rather than being limited to a particular shape and size. Thus it is an object of the present invention to provide a tube-shaped guard with an adjustable diameter so that the guard can be easily secured to fit tightly around a variety of different body shapes and parts. This allows a single guard to be utilized for a wide variety of different applications.

It is another object of the present invention to provide a permanent crease extending between the two ends of the tube so that the tube folds back on itself along the crease. This configuration makes it easy to alter the diameter of the tube as needed for a given area of the body, and it also ensures that the tube remains folded over without bulging so that it can be worn under clothing without discomfort or objectionable appearance. Still further, this configuration allows the tube to be folded so that the diameter of the tube is different throughout the length of the tube, thus enabling it to more fully conform to a portion of the body having a generally tapered shape such as an arm or leg.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention, a device for protecting a portion of the anatomy from exposure to water, bacteria and the like. In such drawings.

DETAILED DESCRIPTION OF THE PREFERRED EMBODIMENT

Figure 2:
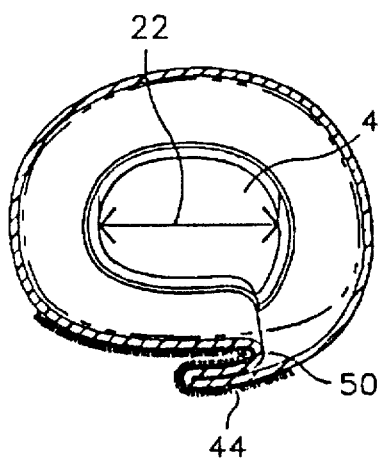
FIG. 2 is a cross-sectional view thereof taken along line 2—2 of FIG. 1, particularly showing the interior of the device.

The above described drawing figures illustrate a body shielding device for protecting a portion of the anatomy from exposure to water, bacteria and the like. There are numerous different possible applications of the present invention, however, for purposes of simplicity the following description will describe it for use in covering a portion of a limb of a human body, although the invention is by no means limited to such application. The guard consists generally of a tapered, open-ended tube 20 constructed of a flexible, water impermeable sheet material, such as vinyl or other plastic sheet stock. The tube 20 has a sidewall 30 with an outer surface 32 that faces generally outwardly and an inner surface 34 that faces generally inwardly. A diameter 22 of the tube 20 is preferably large enough to allow limbs of different sizes to be easily slid through the tube 20. When unfolded (not shown), the tube 20 is preferably of a constant diameter, i.e., diameter 22.

Figure 1:
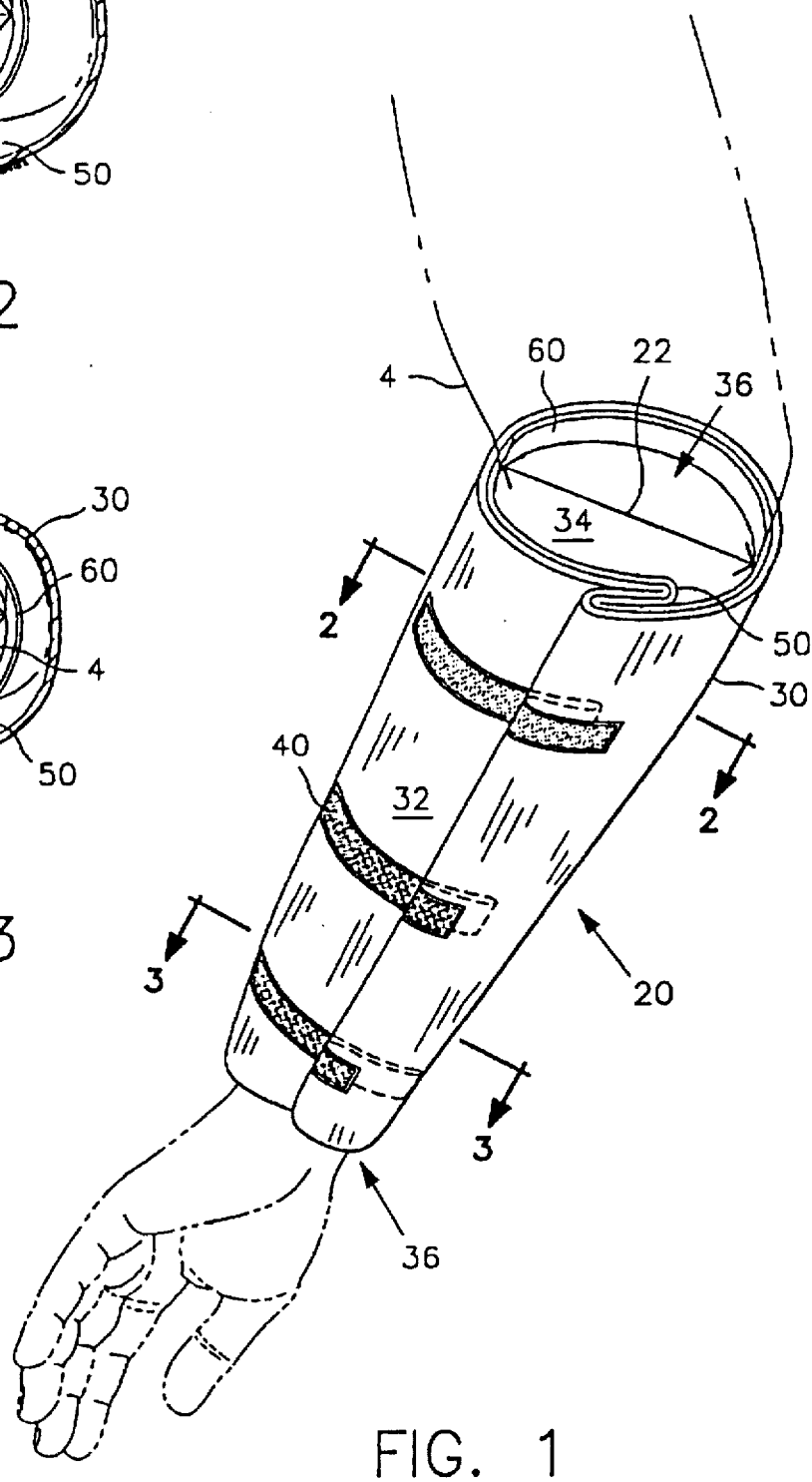
FIG. 1 is a perspective view of the preferred embodiment of the present invention, particularly showing the guard adjusted to fit closely around an arm.

Once the limb 4 is inserted into the tube 20 so that the tube completely covers the portion of the limb to be protected, the diameter 22 of the tube can be decreased so that the tube 20 fits tightly around the limb 4. To accomodate this, the tube sidewall 30 is folded over itself and one or more linear fastening strips 40 are provided on the outer surface 32 of the tube 20 for securing the tube in the folded-over position. As illustrated in FIG. 1, the strips are arranged in mutually spaced apart relationship and are fixed to the outer surface 32 in circumferential orientations. Each of the fastening strips 40 provides, on one side, a means 42 for permanently attaching the strip 40 to the tube 20. On the other side, each strip 40 provides a means 44 for removably fixing a first portion 45A of the fixing means to a second portion 45B of the fixing means 44. Thus, when the tube 20 is folded over, the first and second portions of the fixing means 44 contact and engage with one another so as to keep the tube folded-over until the two portions 45A and 45B are manually disengaged. There are several embodiments of both the permanent attachment means 42 and the removable fixing means 44 well known in the art that may be successfully implemented in the present invention. In one preferred embodiment, the permanent attaching means 42 is an adhesive layer, and the removable fixing means 44 is a distributed surface fastener providing a plurality of mutually interengagable elements. The later described device is commercially available and is used for fastening a wide range of consumer and industrial items. Such an attachment means consists of a flexible base surface layer 45C supporting a large number of outwardly extending protrusions 45D of a shape and size that when two portions of the material are mated they interlock and temporarily bind together much like the well known hook and loop fastener material.

Figure 3:
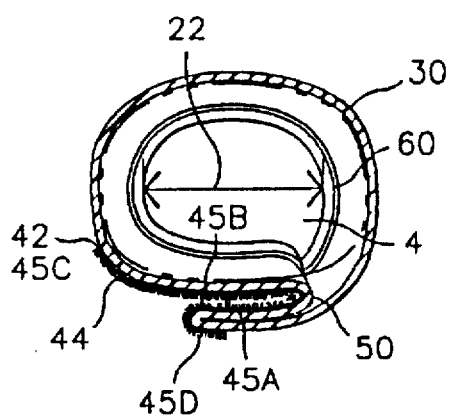
FIG. 3 is a cross-sectional view thereof taken along line 3—3 of FIG. 3.

The sidewall 30 preferably has a permanent crease 50 in it that extends from one open end of the tube to the other, a portion of the sidewall 30 on either side of the crease being folded over itself longitudinally. As illustrated in FIGS. 1–3, the sidewall 30 is preferably permanently folded back on itself along the crease 50 so that the first portion 45A of the removable fixing means 44 is simply engaged with the second portion 45B of the fixing means to maintain the tube 20 in the folded-over position, as clearly illustrated in FIGS. 2 and 3. This inventive configuration is also beneficial in that it allows the tube 40 to be folded over in such a way that the tube diameter 22 is not uniform throughout the length of the tube 40, but rather varies in accordance with the varying contour of the limb 4. This is clearly illustrated in FIGS. 2 and 3, as a greater portion of the tube is folded over in FIG. 3 than in FIG. 2 so that the tube conforms closely to the decreasing size of the limb 4.

An annular rim 60 of water impermeable and compressible material is affixed to the inner surface 34 of the tube 20 adjacent to each of the open ends 36 of the tube. When the tube 20 is folded over so as to fit tightly around the limb 4, the annular rims 60 firmly contact the limb, thus preventing water or the like from seeping into contact with the poriton of the limb being protected. In one embodiment, the compressible material is a closed cell silicone rubber seal.

While the invention has been described with reference to at least one preferred embodiment, it is to be clearly understood by those skilled in the art that the invention is not limited thereto. Rather, the scope of the invention is to be interpreted only in conjunction with the appended claims.

We claim:

1. A wound guard apparatus comprising:

a tube of a flexible, water impermeable, sheet material, the tube having a continuous, unbroken, sidewall with open ends, an outer surface of the sidewall facing generally outwardly therefrom, and an inner surface of the sidewall facing generally inwardly therefrom;

a plurality of linear fastening strips arranged in mutually spaced apart relationship and fixed to the outer surface in circumferential orientations;

each of the fastening strips providing, a means for removable fixing a first selected portion of the removable fixing means to a second selected portion of the removable fixing means; one longitudinal portion of the sidewall being folded over itself about a permanent crease, longitudinally along the apparatus, so as to diminish the inside diameter of the tube for tightly fitting around a limb.

2. The apparatus of claim 1 further including a pair of annular rims of water impermeable and compressible material affixed to the inner surface of the tube, one of the rims being positioned adjacent to each of the open ends of the tube.

3. The apparatus of claim 2 wherein the removable fixing means is a distributed surface fastener providing a plurality of mutually interengagably elements.

4. The apparatus of claim 1 wherein the sidewall has a permanent crease along a longitudinal path extending from one of the open ends to the other of the open ends of the tube, the crease providing for folding of the sidewall.

5. The apparatus of claim 4 wherein the sidewall is permanently folded back on itself along the crease.

\* \* \* \* \*